United States Patent [19]

Phaff et al.

[11] Patent Number: 4,876,357

[45] Date of Patent: Oct. 24, 1989

[54] CHROMOGENIC PHTHALIDES AND AZAPHTHALIDES

[75] Inventors: Rox Phaff, Rheinfelden; Davor Bedekovic, Biel-Benken, both of Switzerland

[73] Assignee: Ciba-Geigy Corporation, Ardsley, N.Y.

[21] Appl. No.: 113,840

[22] Filed: Oct. 26, 1987

[30] Foreign Application Priority Data

Oct. 28, 1986 [CH] Switzerland .......................... 4268/86
Jun. 5, 1987 [CH] Switzerland .......................... 2148/87

[51] Int. Cl.$^4$ ........................................... C07D 405/02
[52] U.S. Cl. ..................................... 548/463; 544/79;
544/80; 544/126; 544/127; 544/130; 544/143;
544/146; 544/153; 544/345; 544/350; 546/89;
546/116; 546/187; 546/196; 546/201; 546/203;
548/456; 549/51; 549/57; 549/307; 549/310
[58] Field of Search ............... 548/456, 463; 544/345,
544/350, 79, 80, 126, 127, 130, 143, 146, 153;
546/89, 116, 187, 196, 201, 203

[56] References Cited

U.S. PATENT DOCUMENTS

| | | | |
|---|---|---|---|
| 4,045,458 | 8/1977 | Kondo et al. | 548/463 X |
| 4,046,776 | 9/1977 | Garner et al. | 548/463 |
| 4,055,358 | 10/1977 | Garner et al. | 548/463 X |
| 4,349,679 | 9/1982 | Garner et al. | 548/456 X |
| 4,351,768 | 9/1982 | Crouse et al. | 548/463 X |
| 4,431,819 | 2/1984 | Schmidt et al. | 548/463 |
| 4,630,080 | 12/1986 | Satake et al. | 503/209 |
| 4,736,027 | 4/1988 | Hung et al. | 548/463 X |

FOREIGN PATENT DOCUMENTS

181646 5/1986 European Pat. Off.

OTHER PUBLICATIONS

Chem. Abstract, 109, 119806b.
Sir Derek Barton, F. R. S. et al., Comp. Org. Chem., vol. 4, pp. 411-414.
Kirk-Othmer, Encyclopedia of Chemical Technology, 3rd ed., vol. 13, (1981), pp. 213-222.
Dictionary of Organic Compounds, 5th Ed., vol. 4, (1982), pp. 3899.

*Primary Examiner*—Richard L. Raymond
*Attorney, Agent, or Firm*—Edward McC. Roberts

[57] ABSTRACT

Chromogenic phthalides and azaphthalides of the formula

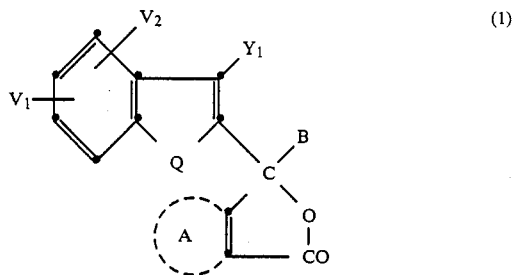

in which $V_1$ and $V_2$ are each, independently of the other, hydrogen, halogen, lower alkyl, lower alkoxy, (lower alkoxy)carbonyl or $-NR_1R_2$, at least one of the radicals $V_1$ and $V_2$ being lower alkoxy or $-NR_1R_2$, A is an unsubstituted or halogen-, cyano-, nitro-, (lower alkyl)-, (lower alkoxy)-, (lower alkyl)thio-, (lower alkyl)amino- or di(lower alkyl)amino-substituted benzene, naphthalene, pyridine, quinoline, pyrazine or quinoxaline ring, B is a substituted phenyl radical of the formula

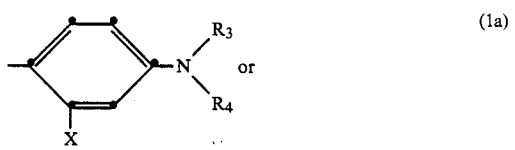

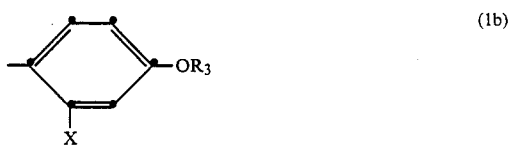

or a 3-indolyl of the formula

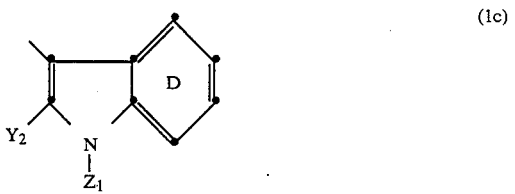

Q is

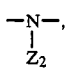

$-S-$ or $-O-$, $R_1$, $R_2$, $R_3$ and $R_4$ are each, independently of the others, hydrogen, unsubstituted or halogen-, hydroxy-, cyano- or (lower alkoxy)-substituted alkyl, cycloalkyl or unsubstituted or ringsubstituted phenalkyl or phenyl, or the substituent pairs ($R_1$ and $R_2$) and ($R_3$ and $R_4$) are each, independently of each other, together with the (Abstract continued on next page.)

nitrogen atom joining them, a five- or six-membered, heterocyclic radical, $Y_1$ is hydrogen, lower alkyl, cycloalkyl, phenalkyl or phenyl, $Y_2$ is hydrogen, lower alkyl or phenyl, $Z_1$ and $Z_2$ are each, hydrogen, unsubstituted or halogen-, hydroxyl-, cyano- or (lower alkoxy)-substituted alkyl acyl or unsubstituted or substituted benzyl, X is hydrogen, halogen, lower alkyl, $C_1$–$C_{12}$-alkoxy, $C_1$–$C_{12}$-acyloxy, benzyl, phenyl, benzyloxy, phenyloxy, halogen-, cyano-, (lower alkyl)- or (lower alkoxy)-substituted benzyl or benzyloxy, or the group —$NT_1T_2$, $T_1$ and $T_2$ are each, independently of the other, hydrogen, lower alkyl, cycloalkyl, unsubstituted or substituted benzyl or acyl and $T_1$ is also unsubstituted or substituted phenyl, and the benzene nucleus D is unsubstituted or substituted. These phthalides and azaphthalides are suitable in particular for use as color formers in pressure- or heat-sensitive recording materials and produce green, greenish blue, greyish blue, blue or violet-blue colors.

9 Claims, No Drawings

CHROMOGENIC PHTHALIDES AND AZAPHTHALIDES

The present invention relates to chromogenic phthalides and azaphthalides, processes for their preparation and their use as colour formers in pressure-sensitive or heat-sensitive recording materials.

The chromogenic compounds according to the invention conform to the general formula

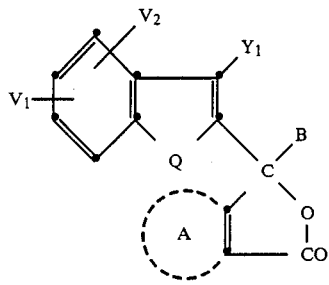
(1)

in which $V_1$ and $V_2$ are each, independently of the other, hydrogen, halogen, lower alkyl, lower alkoxy, (lower alkoxy)carbonyl or $-NR_1R_2$, at least one of the radicals $V_1$ and $V_2$ being lower alkoxy or $-NR_1R_2$, A is an unsubstituted or halogen-, cyano-, nitro-, (lower alkyl)-, (lower alkoxy)-, (Lower alkyl)thio-, (lower alkyl)amino-or di(lower alkyl)amino-substituted benzene, naphthalene, pyridine, quinoline, pyrazine or quinoxaline ring, B is a substituted phenyl radical of the formula

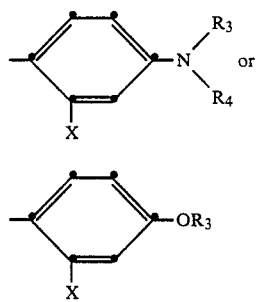

(1a)

(1b)

or preferably a 3-indolyl radical of the formula

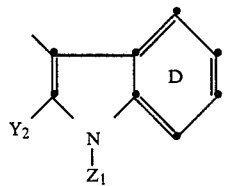
(1c)

Q is

$-S-$ or $-O-$, $R_1$, $R_2$, $R_3$ and $R_4$ are each, independently of the others, hydrogen, unsubstituted or halogen-, hydroxyl-, cyanoor (lower alkoxy)-substituted alkyl having at most 12 carbon atoms, cycloalkyl having 5 to 10 carbon atoms or unsubstituted or halogen-, cyano-, (lower alkyl)- or (lower alkoxy)ringsubstituted phenalkyl or phenyl, or the substituent pairs ($R_1$ and $R_2$) and ($R_3$ and $R_4$) are each, independently of each other, together with the nitrogen atom joining them, a five- or six-membered, preferably saturated, heterocyclic radical, $Y_1$ is hydrogen, lower alkyl, cycloalkyl, phenalkyl or phenyl, $Y_2$ is hydrogen, lower alkyl or phenyl, $Z_1$ and $Z_2$ are each, independently of the other, hydrogen, unsubstituted or halogen-, hydroxyl-, cyano- or (lower alkoxy)-substituted alkyl having at most 12 carbon atoms, acyl having 1 to 12 carbon atoms or unsubstituted or halogen-, cyano-, (lower alkyl)- or (lower alkoxy)- substituted benzyl, X is hydrogen, halogen, lower alkyl, $C_1-C_{12}$-alkoxy, $C_1-C_{12}$-acyloxy, benzyl, phenyl, benzyloxy, phenyloxy, halogen-, cyano-, (lower alkyl)or (lower alkoxy)-substituted benzyl or benzyloxy, or the group $-NT_1T_2$, $T_1$ and $T_2$ are each, independently of the other, hydrogen, lower alkyl, cycloalkyl, unsubstituted or halogen-, cyano-, (lower alkyl)- or (lower alkoxy)-substituted benzyl or acyl having 1 to 12 carbon atoms and $T_1$ is also unsubstituted or halogen-, cyano-, (lower alkyl)- or (lower alkoxy)substituted phenyl, and the benzene nucleus D is unsubstituted or substituted by halogen, cyano, lower alkyl, lower alkoxy, (lower alkoxy)carbonyl, amino, mono(-lower alkyl)amino or di(lower aklyl)amino.

Lower alkyl, lower alkoxy and (lower alkyl)thio are in the definition of the radicals of the phthalides and azaphthalides such groups or group constituents as have 1 to 5, in particular 1 to 3, carbon atoms. Examples of such groups are ethyl, n-propyl, isopropyl, n-butyl, sec.-butyl, amyl or isoamyl in the case of lower alkyl, methoxy, ethoxy, isopropoxy, isobutoxy or tert.-butoxy in the case of lower alkoxy, and methylthio, ethylthio, propylthio or butylthio in the case of (lower alkyl)thio.

Halogen is for example fluorine, bromine or preferably chlorine.

Acyl is in particular formyl, (lower alkyl)carbonyl, for example acetyl or propionyl, or benzoyl. Further acyl radicals can be (lower alkyl)sulfonyl, for example methylsulfonyl or ethylsulfonyl, or phenylsulfonyl.

Benzoyl and phenylsulfonyl can be substituted by halogen, methyl, methoxy or ethoxy. The acyloxy radical in X is for example formyloxy, (lower alkyl)carbonyloxy or benzoyloxy. A $C_1-C_{12}$-alkoxy radical X can be a straightchain or branched group, for example methoxy, ethoxy, isopropoxy, tert.-butoxy, n-hyxyloxy, octyloxy or dodecyloxy.

Q is preferably oxygen. Advantageously, Q can also be $-S-$ or in particular

where $Z'_2$ is hydrogen, $C_1-C_8$-alkyl, acetyl, propionyl, β-cyanoethyl or benzyl. Preference is also given to compounds of the formula (1) in which Q is

and B is a substituted phenyl radical of the formula (1a) or (1b).

Alkyl groups $R_1$, $R_2$, $R_3$, $R_4$, $Z_1$ and $Z_2$ can be straight-chain or branched alkyl radicals. Examples of such alkyl radicals are methyl, ethyl, n-propyl, isopropyl, n-butyl, sec.-butyl, tert.-butyl, amyl, isoamyl, n-hexyl, 2-ethyl-hexyl, n-heptyl, n-octyl, isooctyl, n-nonyl, isononyl or n-dodecyl.

Substituted alkyl radicals $R_1$, $R_2$, $R_3$, $R_4$, $Z_1$ and $Z_2$ are in particular cyanoalkyl, haloalkyl, hydroxyalkyl, alkoxyalkyl each preferably having a total of 2 to 6 carbon atoms, for example β-cyanoethyl, β-chloroethyl, β-hydroxyethyl, β-methoxyethyl or β-ethoxyethyl.

Examples of cycloalkyl R, $Y_1$ or T are cyclopentyl, cycloheptyl or preferably cyclohexyl. The cycloalkyl radicals can contain one or more $C_1$-$C_4$-alkyl radicals, preferably methyl groups, and have a total of 5 to 10 carbon atoms.

Phenalkyl $R_1$, $R_2$, $R_3$, $R_4$ or $Y_1$ preferably has a total of 7 to 9 carbon atoms and generally is a β-methylbenzyl, phenethyl, phenisopropyl or in particular benzyl which can preferably also be ringsubstituted.

Preferred substituents in the benzyl group of R, T, X, Z and Y radicals, in the phenyl group of $R_1$, $R_2$, $R_3$, $R_4$ and $T_1$ and in the benzyloxy group of X are for example halogen, methyl or methoxy. Examples of such araliphatic and aromatic radicals are p-methylbenzyl, o- or p-chlorobenzyl, o- or p-tolyl, xylyl, o-, m- or p-chlorophenyl, o- or p-methoxyphenyl, o- or p-chlorobenzyloxy or o- or p-methylbenzyloxy.

A heterocyclic radical composed of substituent pairs ($R_1$ and $R_2$) and ($R_3$ and $R_4$) together with the shared nitrogen atom is for example pyrrolidino, piperidino, pipecolino, morpholino, thiomorpholino or piperazino, for example N-methylpiperazino. Preferred saturated heterocyclic radicals —$NR_1R_2$ and —$NR_3R_4$ are pyrrolidino, piperidino or morpholino.

The substituents $R_1$, $R_2$, $R_3$ and $R_4$ are preferably cyclohexyl, benzyl, phenethyl, cyano(lower alkyl), for example β-cyanoethyl, or in particular lower alkyl, for example methyl or especially ethyl. —$NR_1R_2$ and —$NR_3R_4$ are preferably also pyrrolidinyl.

X can advantageously be hydrogen, halogen, lower alkyl, for example methyl, benzyloxy, $C_1$-$C_8$-alkoxy, in particular lower alkoxy, for example methoxy, ethoxy, isopropoxy or tert.-butoxy, or an —$NT_1T_2$ group where one of the $T_1$ and $T_2$ is preferably $C_1$-$C_8$-acyl or lower alkyl and the other is hydrogen or lower alkyl. The acyl radical is in this case in particular (lower alkyl)carbonyl, for example acetyl or propionyl. Preferably, X is acetylamino, dimethylamino, benzyloxy or in particular lower alkoxy and especially ethoxy or hydrogen.

The N substituents $Z_1$ and $Z_2$ are preferably benzyl, acetyl, propionyl or in particular alkyl having 1 to 8 carbon atoms, for example methyl, ethyl, n-butyl or especially n-octyl.

$Y_1$ is preferably lower alkyl, for example methyl, ethyl, isopropyl, while $Y_2$ is preferably phenyl or in particular methyl.

$V_1$ is preferably —$NR_1R_2$ or above all lower alkoxy, while $V_2$ is preferably hydrogen, halogen or methyl. $V_1$ is preferably in the 4-position or in particular in the 6-position. A substituent $V_2$ is preferably in the p-position relative to Q (the 5-position).

The ring A is preferably a 1,2-benzo radical which is unsubstituted or substituted by di(lower alkyl)amino, for example dimethylamino, or by four chlorine atoms or bromine atoms. Advantageously, the ring A can also be 1,2-naphthaleno, a 1,8-naphthaleno, a 2,3-pyridino or a 3,4-pyridino radical. The pyridine radical is preferably unsubstituted. Substituents on the pyridine ring are preferably lower alkyl, lower alkoxy or (lower alkyl)thio and also phenyl or phenoxy radicals.

The benzene ring D is preferably not further substituted. Any substituents on D are in particular halogen and lower alkyl, for example methyl.

Practically important phthalides and azaphthalides conform to the formula

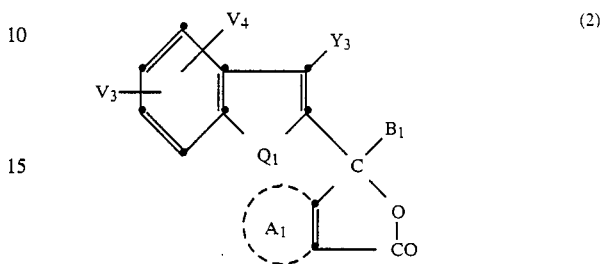 (2)

in which $V_3$ is lower alkoxy or

$V_4$ is hydrogen, halogen or lower alkyl, $A_1$ is an unsubstituted or halogen-, cyano-, (lower alkyl)-, (lower alkoxy)- or di(lower alkyl)amino-substituted benzene or pyridine ring, B is a substituted phenyl radical of the formula

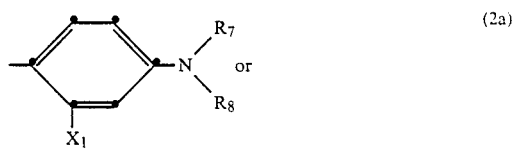 (2a)

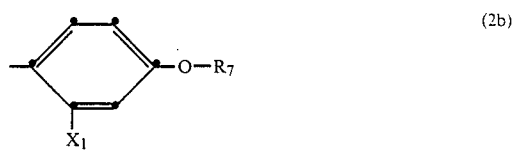 (2b)

or a 3-indolyl radical of the formula

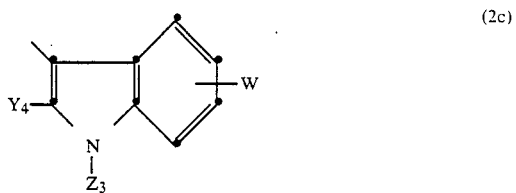 (2c)

$Q_1$ is

—S— or —O—, $R_5$, $R_6$, $R_7$ and $R_8$ are each, independently of the others, unsubstituted or hydroxy-, cyano- or (lower alkoxy)substituted alkyl having at most 12 carbon atoms, $C_5$-$C_6$-cycloalkyl, benzyl, phenethyl or phenyl, or the substituent pairs ($R_5$ and $R_6$) and ($R_7$ and $R_8$) are each, independently of the other, together with the nitrogen atom joining them, pyrrolidino, piperidino or morpholino, $Y_3$ is lower alkyl, $C_5$-$C_6$-cycloalkyl, benzyl, phenethyl or phenyl, $Y_4$ is hydrogen, methyl or phenyl, $Z_3$ and $Z_4$ are each, independently of the other, hydrogen, unsubstituted or cyano- or (lower alkoxy)-substituted $C_1$-$C_8$-alkyl, acetyl, propionyl or benzyl, $X_1$ is hydrogen, halogen, lower alkyl, $C_1$-$C_8$-alkoxy, benzyloxy or the group $-NT_3T_4$, $T_3$ and $T_4$ are each, independently of the other, hydrogen, lower alkyl, (lower alkyl)carbonyl or unsubstituted or halogen-, methyl- or methoxy-substituted benzoyl and W is halogen or preferably hydrogen.

Of the compounds of the formula (2), preference is given to the phthalides in which the ring A is an unsubstituted or halogen- or di(lower alkyl)amino-substituted 1,2-benzo radical. $B_1$ is preferably a substituted phenyl radical of the formula (2a) or (2b). In this context, the R radicals are preferably lower alkyl, and $X_1$ is in particular hydrogen or lower alkoxy. $Y_3$ is preferably methyl.

Of particular interest are phthalides of the formula

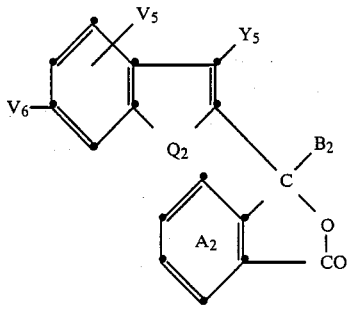 (3)

in which the benzene ring $A_2$ is unsubstituted or substituted by a (lower alkyl)amino or halogen, $B_2$ is an unsubstituted phenyl radical of the formula

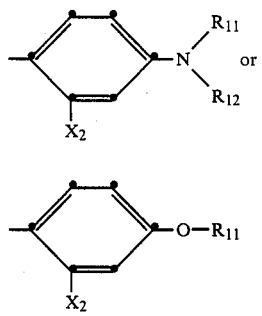 (3a)

(3b)

or a 3-indolyl radical of the formula

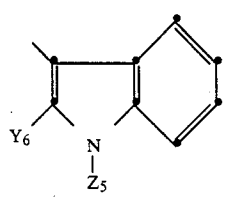 (3c)

$Q_2$ is $-S-$,

or $-O-$, $V_5$ is hydrogen or halogen,
$V_6$ is $-NR_9R$ or lower alkoxy,
$R_9$, $R_{10}$, $R_{11}$ and $R_{12}$ are each, independently of the others, lower alkyl, cyclohexyl or benzyl or the substituent groups $-NR_9R_{10}$ and $NR_{11}R_{12}$ are pyrrolidino, piperidino or morpholino,
$X_2$ is hydrogen, methyl, lower alkoxy, benzyloxy, acetylamino, propionylamino, benzoylamino or di(-lower alkyl)amino,
$Y_5$ is lower alkyl, for example methyl,
$Y_6$ phenyl or in particular methyl, and
$Z_5$ and $Z_6$ are each, independently of the other, hydrogen, alkyl 1 to 8 carbon atoms or benzyl.

Of these compounds of the formula (3), particular preference is given to those in which $A_2$ is an unsubstituted or dimethylamino-substituted 1,2-benzo radical,
$B_2$ is a substituted phenyl radical of the formula (3a) or the 3-indolyl radical of the formula (3c),
$Q_2$ is $-O-$,
$V_5$ is hydrogen or chlorine,
$V_6$ is $-NR_9R_{10}$,
$R_9$ is methyl, ethyl or cyclohexyl,
$R_{10}$ is methyl or ethyl or $-NR_9R_{10}$ is pyrrolidinyl,
$R_{11}$ and $R_{12}$ are each methyl or ethyl or $-NR_{11}R_{12}$ is pyrrolidinyl,
$Y_5$ is methyl or ethyl,
$Y_6$ is methyl, $X_2$ is hydrogen, methoxy or ethoxy and
$Z_5$ is methyl, ethyl, n-butyl, hexyl or in particular n-octyl.

Preference is also given to compounds of the formula (3) in which
$A_2$ is an unsubstituted or dimethylamino-substituted 1,2-benzo radical,
$B_2$ is a substituted phenyl radical of the formula (3a) or (3b),
$Q_2$ is

$V_5$ is hydrogen or chlorine,
$V_6$ is $-NR_9R_{10}$,
$R_9$ is methyl, ethyl or cyclohexyl,
$R_{10}$ is methyl or ethyl or $NR_9R_{10}$ is pyrrolidinyl
$R_{11}$ and $R_{12}$ are each methyl or ethyl or $-NR_{11}R$ is pyrrolidinyl,
$Y_5$ is methyl or ethyl,
$X_2$ is hydrogen, methoxy or ethoxy and
$Z_6$ is $C_1$-$C_8$-alkyl, in particular methyl or ethyl.

Very particular preference is given to compounds of the formula (3) in which
$A_2$ is an unsubstituted or dimethylamino-substituted 1,2-benzo radical,
$B_2$ is a substituted phenyl radical of the formula (3a),
$Q_2$ is

$V_5$ is hydrogen or chlorine, $V_6$ is lower alkoxy, especially methoxy, $R_{11}$ and $R_{12}$ are each methyl, ethyl or $-NR_{11}R_{12}$ is pyrrolidinyl, $Y_5$ is methyl or ethyl, $X_2$ is hydrogen, methoxy or ethoxy and $Z_6$ is $C_1$-$C_8$-alkyl, in particular methyl, ethyl or n-octyl.

The inventious phthalides and azaphthalides of the formulae (1) to (3) are novel chromogenic compounds and can be prepared by methods known per se.

A process for preparing the compounds of the formula (1) comprises reacting in any desired order one mole of an anhydride of the formula

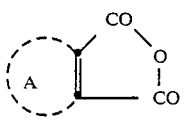

with one mole of a compound of the formula

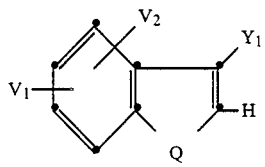 (5)

and one mole of a compound of the formula

B—H  (6)

when, in the formulae (4), (5) and (6), A, B, Q, $V_1$, $V_2$, and $Y_1$ are as defined above.

Advantageously, the lactones according to the invention are prepared by reacting a compound of the formula (5) with a compound of the formula

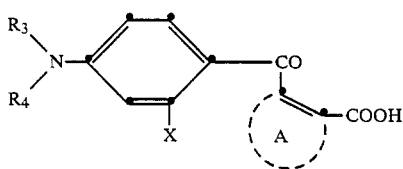 (7)

or of the formula

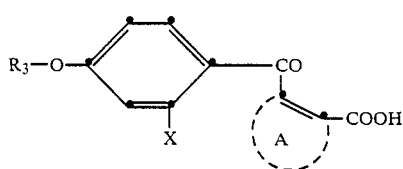 (8)

or of the formula

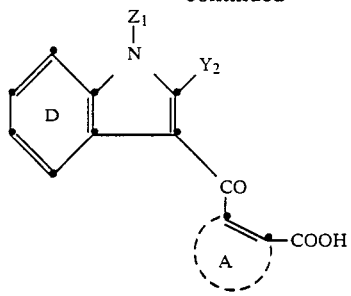 (9)

where, in the formulae (7), (8) and (9), A, D, $R_3$, $R_4$, X, $Z_1$ and $Y_2$ are as defined above.

The reactions are preferably carried out by making the reaction components react in the presence of an acid dehydrating agent at a temperature of 20° C. to 140° C. Examples of such condensing agents are acetic anhydride, zinc chloride, sulfuric acid, phosphoric acid and phosphorus oxychloride.

The end product of the formula (1) is isolated in a generally known method by bringing the reaction mixture to a pH of at least 6, preferably 7 to 11, for example with alkalis, e.g. alkali metal hydroxides, ammonia, alkali metal carbonates or alkalimetalbicarbonates and separating off the resulting precipitate, washing and drying or treating with suitable organic solvents, for example methanol, isopropanol, benzene, chlorobenzene or in particular toluene or toluene/methanol. If isomeric mixtures of azaphthalides are obtained, the individual 4- and 7-azaphthalides and the 5- and 6-azaphthalides are separated by chromatography and/or recrystallization.

The starting compounds of the formula (5) are novel or are described for example in No. EP-A-106,800. In general, they can be obtained for example by reacting a 3-aminobenzene compound of the formula

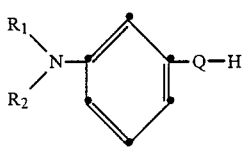 (10)

with a compound of the formula (11) $Y_1$-CO-$CH_2$-Hal, where Hal is halogen, or with a corresponding acetal thereof, for example chloroacetone or 2-chloro-1,1-diethoxyethane, in the presence of a base, for example potassium carbonate, and is in the absence or presence of an organic solvent, for example dimethylformamide. In the formulae (10) and (11), $R_1$, $R_2$, Q and $Y_1$ are as defined above.

The starting materials of the formula (4), (6), (7) and (9) are described for example in German Offenlegungsschriften Nos. DE-A-2,265,233, DE-A-2,514,934, DE-A-3,247,059, DE-A-3,319,978 and DE-A-3,600,725 and in European Patent Applications Nos. EP-A-82,822 and EP-A-140,839.

The phthalides and azaphthalides of the formulae (1) to (3) are normally colourless or at most slightly coloured. If these colour formers are contacted with a preferably acid developer, i.e. an electron acceptor, may produce, depending on the definition of A, B and Q and the developer used, deep green, greenish blue, blue or violetblue colours which are fast to sublimation and light. Greendeveloping colour formers, in addition, exhibit absorption in the IR region as well. The corresponding script image can thus be read by machine, for example using a laser. The phthalides and azaphthalides of the formulae (1) to (3) are also useful in a mixture with one or more other known colour formers, for example 3,3-(bis aminophenyl)-phthalides, (3,3-bisindolyl)-phthalides, 3-aminofluorans, 2,6-diaminofluorans, 2,6-diamino-3-methylflourans, leucoauramins, spiropyrans, spirodipyrans, chromenopyrazols, chromenoindols, phenoxazines, phenothiazines, quinazolines, rhodaminelactams, carbazolylmethanes or further triarylmethane leuco dyes to produce blue, navy, grey or black dyeings.

The phthalides and azaphthalides of the formulae (1) and (3) exhibit an excellent colour intensity and light fastness not only on activated clays but also on phenolic substrates. They are suitable in particular for use as rapidly developing colour formers for use in a heat-sensitive or in particular pressure-sensitive recording material which can be not only a copying but also a registering material. They are pH stable and highly soluble in capsule oils. After exposure in the CB sheet they are substantially stable to CB decline (decrease in colour strength).

A pressure sensitive material consists for example of at least one pair of sheets which contain at least one colour former of the formulae (1) to (3) dissolved in an organic solvent and an electron acceptor as developer.

Typical examples of such developers are active clay substances, such as attapulgite clay, acid clay, bentonite, montmorillonite, activated clay, for example acid-activated bentonite or montmorillonite, and also zeolite, halloysite, silica, alumina, aluminium sulfate, aluminium phosphate, zinc chloride, zinc nitrate, activated kaolin or any other desired clay or acidic organic compound, for example unsubstituted or ring-substituted phenols, resorcinols, salicylic acid e.g. 3,5-bis-($\alpha,\alpha$-dimethylbutyl)salicylic acid or 3,5-bis-($\alpha$-methylbenzyl)-salicylic acid, or salicylic acid esters and metal salts thereof for example zinc salts, and also an acidically reacting polymeric material, for example a phenolic polymer, an alkylphenol-acetylene resin, a maleic acid-rosin resin or a partially or completely hydrolysed polymer of maleic acid anhydride with styrene, ethylene or vinyl methyl ether, or carboxymethylene. It is also possible to use mixtures of the monomeric and polymeric compounds mentioned. Preferred developers are acid-activated bentonite, zinc salicylates or the condensation products of p-substituted phenols with formaldehyde. The latter can also be modified with zinc.

The developers can additionally be used in a mixture with basically completely or substantially unreactive pigments or further auxiliary substances such as silica gel or UV absorbers, for example 2-(2'hydroxyphenyl)-benzotriazoles. Examples of such pigments are:

talc, titanium dioxide, aluminium oxide, aluminium hydroxide, zinc oxide, chalk, clays such as kaolin, and also organic pigments, for example ureaformaldehyde condensates (BET surface area 2–75 m$^2$/g) or melamine-formaldehyde condensation products.

The colour former produces a coloured marking in those areas where it comes into contact with the electron acceptor. To prevent premature activation of the colour formers present in the pressure-sensitive recording material, the colour formers are generally separated from the electron acceptor. This can advantageously be done by incorporating the colour formers in foamlike, spongelike or honeycomblike structures. Preferably, the colour formers are enclosed in microcapsules which in general are disintegrable by pressure.

On disintegration of the capsules by pressure, for example by means of a pencil, the colour former solution is transferred to an adjacent sheet coated with an electron acceptor, thereby producing a coloured area. The colour results from the dye which is formed in the course of the process and which absorbs in the visible region of the electromagnetic spectrum.

Colour formers are preferably encapsulated in the form of solutions in organic solvents. Examples of suitable solvents are preferably non-volatile solvents, for example polyhalogenated paraffin or diphenyl, such as chloroparaffin, monochlorodiphenyl or trichlorodiphenyl, and also tricresyl phosphate, di-n-butyl phthalate, dioctyl phthalate, trichlorobenzene, trichloroethyl phosphate, aromatic ethers, such as benzyl phenyl ether, hydrocarbon oils, such as paraffin or kerosine, for example derivatives of diphenyl, naphthalene or terphenyl which have been alkylated for example with isopropyl, isobutyl, sec.-butyl or tert.-butyl, dibenzyltoluene, partially hydrogenated terphenyl, mono- to tetra-$C_1$-$C_3$-alkylated phenylalkanes, dodecylbenzene, benzylated xylenes, or further chlorinated or hydrogenated, condensed aromatic hydrocarbons. Frequently, mixtures are used of different solvents, in particular mixtures of paraffin oils or kerosine and diisopropylnaphthalene or partially hydrogenated terphenyl to obtain optimum solubility for the colour former, a rapid and deep coloration and a favourable viscosity for microencapsulation. In encapsulation the phthalides and azaphthalides according to the invention have a remarkably high pH-stability, for example in the pH range from 4 to 10.

The capsule walls can be formed evenly around the droplets of the colour former solution by coazervation, and the encapsulation material is described for example in U.S. Pat. No. 2,800,457. The capsules can preferably also be formed from an amino resin or modified amino resins by polycondensation, as described in British Patents Nos. 989,264, 1,156,725, 1,301,052 and 1,355,124. Similarly suitable are microcapsules formed by interface polymerization, for example capsules made of polyester, polycarbonate, polysulfonamide, polysulfonate, but in particular polyamide or polyurethane.

The microcapsules containing colour formers of the formulae (1) to (3) can be used for producing pressure-sensitive copying materials of all the various known types. The various systems essentially differ from one another in the arrangement of the capsules and of the colour reactants and in the base material.

Preference is given to an arrangement where the encapsulated colour former is present in the form of a layer on the back of a transfer sheet and the electron acceptor is present in the form of a layer on the front of a receiver sheet.

In another arrangement of the constituents, the microcapsules containing the colour former and the developer are present in or on the same sheet in the form of one or more individual layers or in the paper pulp.

The capsules are preferably attached to the base by means of a suitable binder. Since paper is the preferred base material, this binder chiefly comprises paper-coating agents, such as gum arabic, polyvinyl alcohol, hydroxymethyl cellulose, casein, methyl cellulose, dextrose, starch, starch derivatives, or polymer latexes. The latter are for example butadienestyrene copolymers or acrylic homopolymers or copolymers.

The paper used comprises not only standard papers made of cellulose fibres but also papers in which the cellulose fibres have been (partly or wholly) replaced by fibres made of synthetic polymers.

The compounds of the formulae (1) to (3) can also be used as colour formers in a thermoreactive recording material. The thermoreactive recording material generally contains at least one base material, a colour former, an electron acceptor and can, if desired, also contain a binder and/or wax.

Thermoreactive recording systems comprise for example heat-sensitive recording and copying materials and papers. These systems are used for example for recording data signals, for example in electronic computers, teleprinters or telex machines or in recording equipment and measuring instruments, for example electrocardiographs. Image production (marking) can also be effected manually by means of a hot pen. A further way of producing markings by means of heat is a laser beam.

The thermoreactive recording material can be configured in such a way that the colour former is dissolved or dispersed in a binder layer and the developer is dissolved or dispersed in the binder in a second layer. In another option, both the colour former and the developer are dispersed in one and the same layer. The binder is softened in specific areas by means of heat, the colour former comes into contact with the electron acceptor in these areas to which heat is applied, and the desired colour develops at once.

Suitable developers are the same electron acceptors as used in pressure-sensitive papers. Examples of developers are the previously mentioned clay minerals and phenolic resins or even phenolic compounds as described for example in DE Patent No. 1,251,348, e.g. 4-tert.-butylphenol, 4-phenylphenol, methylene-bis(p-phenylphenol), 4-hydroxydiphenyl ether, α-naphthol, β-naphthol, methyl or benzyl 4-hydroxybenzoate, 4-hydroxydiphenyl sulfone, 4'-hydroxy-4-methyldiphenyl sulfone, 4'-hydroxy-4-isopropoxydiphenyl sulfone, 4-hydroxyacetophenone, 2,2'-dihydroxydiphenyl, 4,4'-cyclohexylidenediphenol, 4,4'-isopropylidenediphenol, 4,4'-isopropylidenebis-(2-methylphenol), an antipyrine complex of zinc thiocyanate, a pyridine complex of zinc thiocyanate, 4,4-bis-(4-hydroxyphenyl)valeric acid, hydroquinone, pyrogallol, phloroglucine, p-, m- or o-hydroxy-benzoic acid, gallic acid, 1-hydroxy-2-naphthoic acid, and also boric acid or organic, preferably aliphatic, dicarboxylic acids, e.g. tartaric acid, oxalic acid, maleic acid, citric acid, citraconic acid or succinic acid.

Preferably, the thermoreactive recording material is prepared by means of meltable, film-forming binders. These binders are normally water-soluble, while the phthalides and the azaphthalides and the developer are sparingly soluble or insoluble in water. The binder should be capable of dispersing and fixing the colour former and the developer at room temperature.

Heat softens or melts the binder, so that the colour former comes into contact with the developer and a colour can develop. Water-soluble or at least water-swellable binders are for example hydrophilic polymers, such as polyvinyl alcohol, polyacrylic acid, hydroxyethylcellulose, methylcellulose, carboxymethylcellulose, polyacrylamide, polyvinylpyrrolidone, gelatin, starch or etherified maize starch.

If the colour former and the developer are present in two separate layers, it is possible to use water-insoluble binders, i.e. binders which are soluble in non-polar or only slightly polar solvents, for example natural rubber, synthetic rubber, chlorinated rubber, alkyd resins, polystyrene, styrene/butadiene copolymers, polymethyl acrylates, ethylcellulose, nitrocellulose, and polyvinylcarbazole. However, the preferred arrangement is that where the colour former and the developer are present in a water-soluble binder in a single layer.

The thermoreactive layers can contain further additives. To improve the whiteness, to facilitate printing on the papers and to prevent sticking of the hot pen, these layers can contain for example talc, titanium dioxide, zinc oxide, aluminium hydroxide, calcium carbonate, (for example chalk) clays or even organic pigments, for example ureformaldehyde polymers. To bring about that the colour is formed only within a limited temperature range, it is possible to add substances, such as urea, thiourea, diphenylthiourea, acetamide, acetanilide, benzenesulfanilide, stearamide, phthalic anhydride, metal stearates, for example zinc stearate, phthalicnitrile, dimethyl terephthalate or other corresponding meltable products, which induce the simultaneous melting of colour former and developer. Preferably, the thermographic recording materials contain waxes, for example carnauba wax, montana wax, paraffin wax, polyethylene wax, condensates of higher fatty acid amides and formaldehyde and condensates of higher fatty acids and ethylenediamine.

A further use of compounds of the formulae (1) to (3) is the preparation of a colour image by means of photocurable microcapsules as described for example in DE Offenlegungsschrift No. 3,247,488.

In the examples which follow, the stated percentages are by weight, unless otherwise stated.

EXAMPLE 1:

3.5 g of (2-methyl-1-n-octylindol-3-yl)-(2-carboxyphenyl)ketone and 1.6 g of 6-dimethylamino-3-methylbenzofuran are suspended in 45 ml of acetic anhydride and heated to 40° C. After 2 hours the reaction product is poured onto ice, basified with concentrated sodium hydroxide solution and filtered off. The crude product is recrystallized from toluene/methanol to give 3.25 g of the 3-(6-dimethylamino-3-methyl-benzofuran-2-yl)-3-(2-methyl-1-n-octylindol-3-yl)phthalide compound of the formula

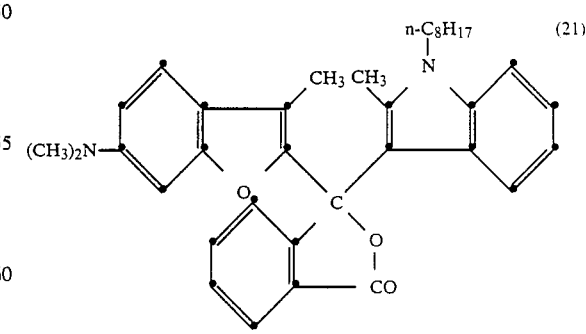

having a melting point of 157°–158° C. The phthalide compound gives a green colour on acid-modified silica gel.

The 6-dimethylamiono-3-methylbenzofuran used in Example 1 is prepared as follows:

140 g of 3-dimethylaminophenol are dissolved in 700 ml of dimethylformamide. 152 g of potassium carbonate and 28 g of potassium iodide are added. 101.8 g of chloroacetone are then added dropwise in the course of one hour; afterwards the mixture is stirred at room temperature for 20 hours. The reaction solution is filtered and the dimethylformamide and unconverted chloroacetone are distilled off (30° C., 1 mm Hg). Water is added to the residue, and the mixture is basified with concentrated sodium hydroxide solution and filtered. The crude product is taken up in 1 litre of ethanol, 115 ml of concentrate hydrochloric acid are added, and the mixture is heated to 80° C. 40 hours later the mixture is cooled down, treated with active carbon and filtered. The alcohol is removed, water is added to the residue, and the mixture is basified with concentrated sodium hydroxide solution. The crude product is filtered off and recrystallized from a mixture of hexane and diethyl ether (10:1) to give 36 g of 6-dimethylamino-3-methyl-benzofurane.

Example 1 is repeated using appropriate starting materials to obtain the phthalides of the formula

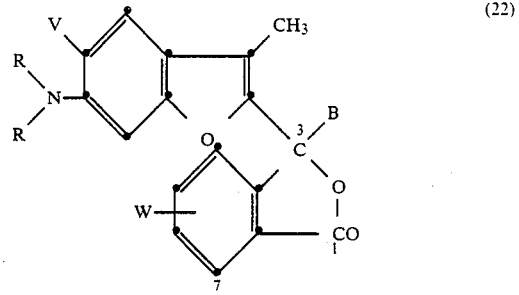

(22)

listed in the table below.

TABLE 1

| Example | —NRR | V | W | B | Melting point/°C. | Colour |
|---|---|---|---|---|---|---|
| 2 | —N(C$_2$H$_5$)$_2$ | H | H | 3-methyl-1-(n-C$_8$H$_{17}$)-indol-2-yl | 149–150 | green |
| 3 | azetidin-1-yl (—N⟨⟩) | Cl | H | 3-methyl-1-(n-C$_8$H$_{17}$)-indol-2-yl | 77–85 | green |
| 4 | —N(C$_2$H$_5$)$_2$ | H | H | 3-methyl-1-(C$_2$H$_5$)-indol-2-yl | 189–190 | green |
| 5 | —N(CH$_3$)$_2$ | CH$_3$ | H | 3-methyl-1-(n-C$_8$H$_{17}$)-indol-2-yl | | green |
| 6 | azetidin-1-yl (—N⟨⟩) | Cl | 6-N(CH$_3$)$_2$ | 4-(N(CH$_3$)$_2$)phenyl | 98–130 | turquoise |
| 7 | —N(CH$_3$)$_2$ | H | 6-N(CH$_3$)$_2$ | 4-(N(CH$_3$)$_2$)phenyl | 148 | blue |

TABLE 1-continued

| Example | —NRR | V | W | B | Melting point/°C. | Colour |
|---|---|---|---|---|---|---|
| 8 | —N(azetidine) | $CH_3$ | 6-$N(CH_3)_2$ | phenyl-$N(CH_3)_2$ | | blue |
| 9 | —$N(C_2H_5)_2$ | H | 6-$N(CH_3)_2$ | phenyl-$N(CH_3)_2$ | 200–201 | turquoise |
| 10 | —$N(C_2H_5)_2$ | H | H | phenyl with $N(C_2H_5)_2$ and $OC_2H_5$ | | blue |
| 11 | —$N(C_2H_5)_2$ | H | H | phenyl with $N(C_2H_5)_2$ and $OCH_3$ | 71–80 | green |
| 12 | —$N(C_2H_5)_2$ | H | 6-$N(CH_3)_2$ | phenyl-$OCH_3$ | 190–192 | bluish grey |

Example 1 is repeated using appropriate starting materials to prepare also the colour formers of the formula (23)

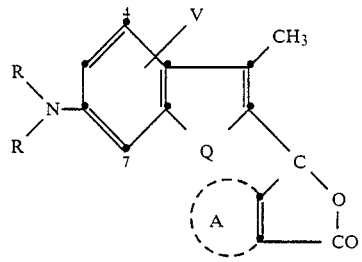

(23)

listed in table 2.

TABLE 2

| Example | —NRR | V | Q | A | B | Melting point/°C. | Colour |
|---|---|---|---|---|---|---|---|
| 13 | —$N(CH_3)_2$ | H | —N—$C_2H_5$ | $(CH_3)_2N$-phenyl | phenyl-$N(CH_3)_2$ | 207–208 | greyish blue |
| 14 | —$N(CH_3)_2$ | 7-$CH_3$ | —N—$CH_3$ | $(CH_3)_2N$-phenyl | phenyl-$N(CH_3)_2$ | | blue |
| 15 | —$N(CH_3)_2$ | 5-$CH_3$ | —S— | $(CH_3)_2N$-phenyl | phenyl-$N(CH_3)_2$ | 116–152 | blue |

TABLE 2-continued

| Example | —NRR | V | Q | A | B | Melting point/°C. | Colour |
|---|---|---|---|---|---|---|---|
| 16 | —N(CH₃)₂ | H | —S— | (CH₃)₂N-C₆H₃(CH₃)- | -C₆H₃(CH₃)-N(CH₃)₂ | 266–267 | blue |
| 17 | —N(CH₃)₂ | 4-OCH₃ | —O— | (CH₃)₂N-C₆H₃(CH₃)- | -C₆H₃(CH₃)-N(CH₃)₂ | | blue |
| 18 | —N(CH₃)₂ | 4-N(CH₃)₂ | —N(CH₃)— | (CH₃)₂N-C₆H₃(CH₃)- | -C₆H₃(CH₃)-N(CH₃)₂ | | blue |
| 19 | —N(CH₃)₂ | 4-N(C₂H₅)₂ | —O— | C₆H₃(CH₃)- | 1-ethyl-2-methylindol-3-yl | | green |
| 20 | —N(CH₃)₂ | H | —S— | C₆H₃(CH₃)- | 1-ethyl-2-methylindol-3-yl | 91–109 | green |
| 21 | —N(CH₃)₂ | 7-CH₃ | —N(CH₃)— | C₆H₃(CH₃)- | 3-OC₂H₅-4-N(C₂H₅)₂-C₆H₃- | | green |
| 22 | —N(CH₃)₂ | 4-OCH₃ | —S— | C₆H₃(CH₃)- | 3-OC₂H₅-4-N(C₂H₅)₂-C₆H₃- | | green |
| 23 | aziridin-1-yl | 5-Cl | —O— | 2,3,4,5-tetrachlorophenyl | 1-ethyl-2-methylindol-3-yl | | green |

TABLE 2-continued
| Example | —NRR | V | Q | A | B | Melting point/°C. | Colour |
|---|---|---|---|---|---|---|---|
| 24 | —N(CH₃)₂ | H | —S— | 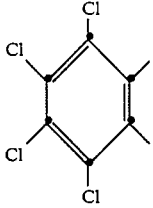 | 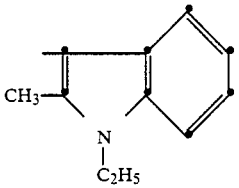 | | green |
| 25 | —N(C₂H₅)₂ | H | 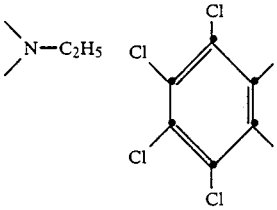 | 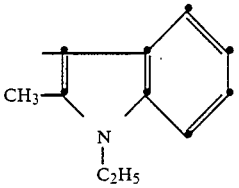 | 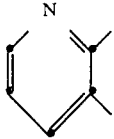 | | green |
| 26 | —N(C₂H₅)₂ | H | —O— | 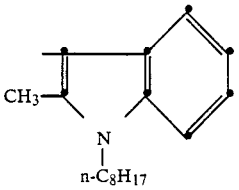 | 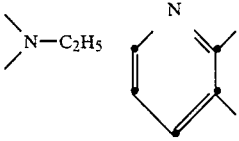 | 71–103 | green |
| 27 | —N(CH₃)₂ | H | 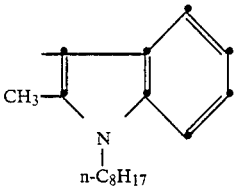 | 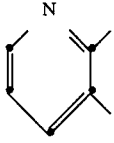 | 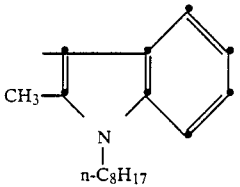 | 141–142 | green |
| 28 | —N(C₂H₅)₂ | 4-OCH₃ | —S— | 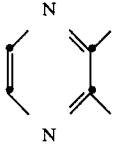 | | | green |
| 29 | —N(C₂H₅)₂ | H | —O— | 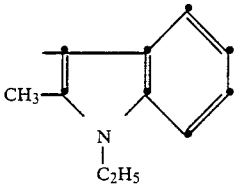 | | | green |
| 30 | —N(C₂H₅)₂ | 7-CH₃ | 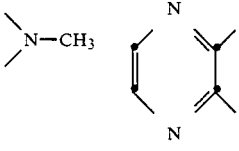 | 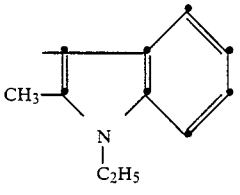 | | | green |

TABLE 2-continued
| Example | —NRR | V | Q | A | B | Melting point/°C. | Colour |
|---|---|---|---|---|---|---|---|
| 31 | —N(CH$_3$)$_2$ | H | —O— | 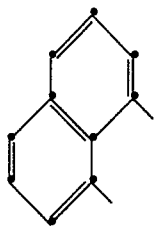 | 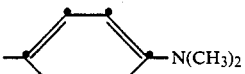 | | green |
| 32 | —N(C$_2$H$_5$)$_2$ | H | —O— | 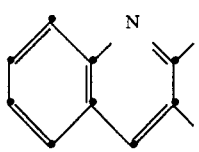 | 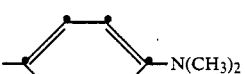 | | green |
| 33 | —N(CH$_3$)$_2$ | H | —N—C$_2$H$_5$ | 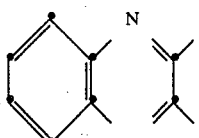 | 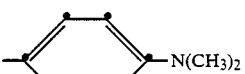 | | green |
| 34 | —N(CH$_3$)$_2$ | H | —N—C$_2$H$_5$ | 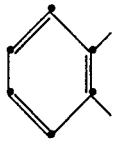 | 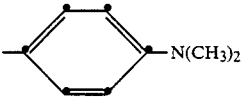 | 197–198 | green |
| 35 | —N(CH$_3$)$_2$ | H | —N—C$_2$H$_5$ | 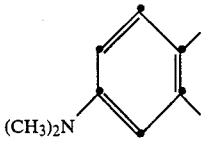 | 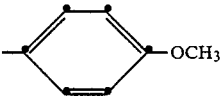 | 239–240 | greyish blue |
| 36 | —N(CH$_3$)$_2$ | H | —N—C$_2$H$_5$ | 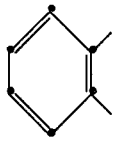 |  | 198–199 | bluish grey |
| 37 | —N(CH$_3$)$_2$ | H | —N—C$_2$H$_5$ | 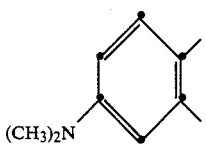 | 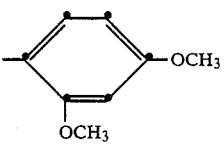 | 228–229 | greyish blue |
| 38 | —N(CH$_3$)$_2$ | H | —N—C$_2$H$_5$ | 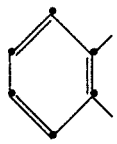 | 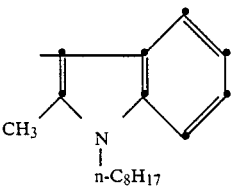 | 107–110 | green |

TABLE 2-continued

| Example | —NRR | V | Q | A | B | Melting point/°C. | Colour |
|---|---|---|---|---|---|---|---|
| 39 | —N(C₂H₅)₂ | H | —O— | (2,3,4,5-tetrachlorophenyl) | (1-ethyl-2-methylindol-3-yl) | 230 decomposition | green |

EXAMPLE 40:

3.12 of 4,4'-bis-dimethylaminobenzophenone-2-carboxylic acid and 1.9 g of 1-ethyl-3-methyl-6-methoxyindol are stirred at 40° C. in 30 ml of acetic anhydride for 3 hours. The reaction mixture is poured onto ice, the resulting mixture is basified with NaOH and extracted with toluene. The organic phase is separated off, and treated with active carbon, dried and evaporated. The residue is decrystallized once from diethyl ether and once from toluene to give 3.35 g of 3-(4-dimethylaminophenyl)-3-(1-ethyl-3-methyl-6-methoxyindol-2-yl)-6-dimethylaminophthalide of the formula

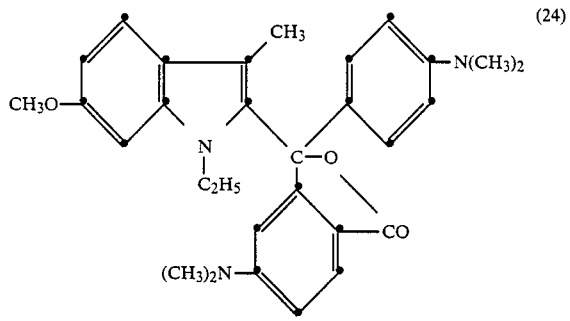

(24)

melting point 224°–225° C. On acid clay this compound produces a blue colour.

The 1-ethyl-3-methyl-6-methoxyindol used is prepared as follows: 4.6 g of 3-methyl-6-methoxyindole [Chem. ber. 98, 1727 (1965)] are presented in 29 ml of dimethyl sulfoxide. 6.6 ml of 10n aqueous KOH are then added, and 3.25 g of ethyl bromide are added dropwise at 20° C. in the course of 30'. 1 hour later the reaction mixture is poured onto water and extracted with toluene. Chromatography over silica gel (hexane/ether 5:1) gives 3.9 g of 1-ethyl-3-methyl-6-methoxyindol in the form of an oil.

EXAMPLE 41:

3 g of 4-dimethylamino-4'-methoxybenzophenone-2-carboxylic acid and 1.9 g of 1-ethyl-3-methyl-6-methoxyindole are stirred at 40° C. in 30 ml of acetic anhydride for 4 hours. This is followed by discharging onto ice, basifying with sodium hydroxide solution and extraction with toluene. The toluene phase is treated with active carbon, dried over magnesium sulfate and evaporated to give 4.45 g of 3-(4-methoxyphenyl)-3-(1-ethyl-3-methyl-6-methoxyindol-2-yl)-6-dimethylaminophtalide of the formula

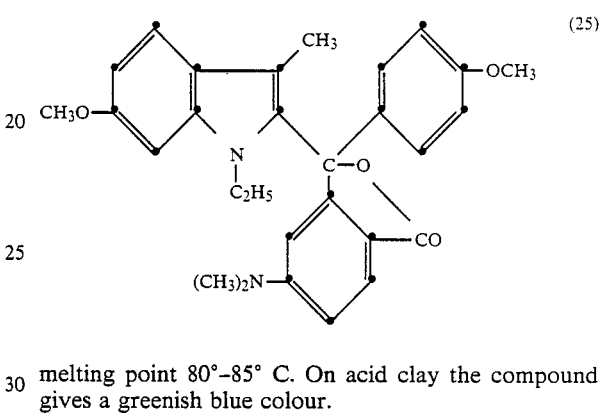

(25)

melting point 80°–85° C. On acid clay the compound gives a greenish blue colour.

EXAMPLE 42:

1.91 g of 4-dimethylamino-3-methyl-benzothiophene are added to 30 ml of acetic anhydride. 3.12 g of 4,4'-bis-dimethylaminobenzophenone-2-carboxylic acid are added. The mixture is heated at 45° C. for 7 hours, and then cooled down, discharged onto ice and basified with sodium hydroxide. The mixture is extracted with toluene, and the toluene phase is treated with active carbon, dried and evaporated. The column chromatography of the residue over silica gel gives 3.75 g of a compound of the formula

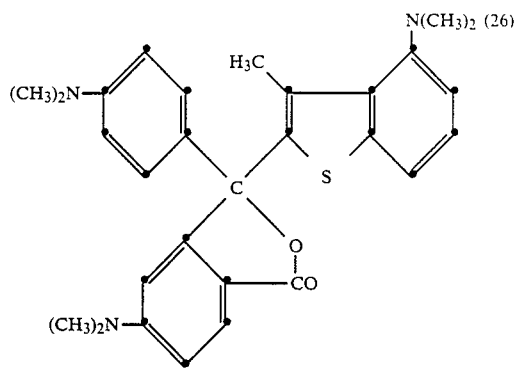

(26)

melting point 116°–128° C. On acid clay this compound produces a blue colour.

EXAMPLE 43:

3.78 g of (2-methyl-1-n-octylindol-3-yl)-(2-carboxyphenyl) ketone and 1.81 g of 1-ethyl-3-methyl-6-methoxyindole are stirred at 40° C. in 30 ml of acetic anhydride for 8 hours. The reaction mixture is poured onto ice, basified with concentrated sodium hydroxide solution and extracted with toluene. The toluene phase is washed once with water, separated off, treated with active carbon, dried over sodium sulfate and evaporated. Recrystallization from a 3:2 mixture of hexane and diethyl ether gives 2.2 g of a compound of the formula

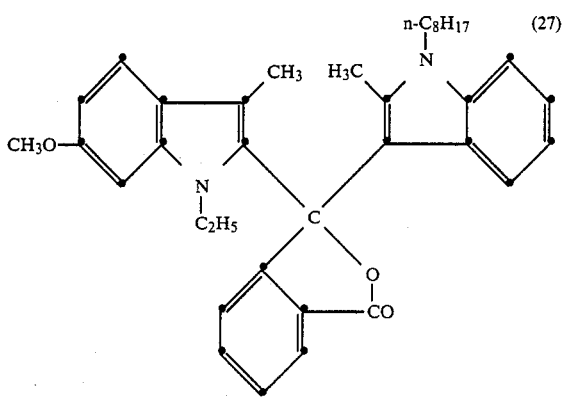

melting point 95°–140° C. On acid clay this compound produces a blue colour.

EXAMPLE 44:

2.58 g of (4-dimethylaminophenyl)-(2-carboxyphenyl) ketone and 1.81 g of 1-ethyl-3-methyl-6-methoxyindole are stirred at 40° C. in 30 ml of acetic anhydride for 4 hours. The reaction mixture is poured onto ice, basified with concentrated sodium hydroxide solution and extracted with toluene. The organic phase is washed with water, treated with active carbon, dried over sodium sulfate and evaporated. The residue is suspended in dimethyl ether, filtered off and dried to five 2.85 g of a compound of the formula

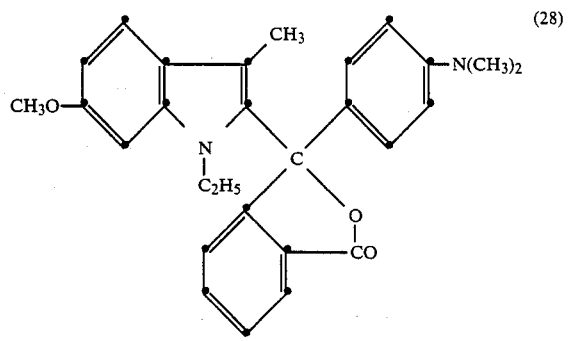

melting point 177°–178° C. On acid clay this compound produces a turquoise colour.

EXAMPLE 45:

Preparation of a pressure sensitive copying paper

A solution of 3 g of the phthalide of the formula (21) (Example 1) in 80 g of diisopropylnaphthalene and 17 g of kerosine is microencapsulated in a conventional manner with gelatin and gum arabic by coacervation, mixed with a starch solution and coated onto a sheet of paper. A second sheet of paper is coated on the front with active clay for use as colour developer. The first sheet containing the colour former and the sheet of paper coated with the colour developer are placed on top of each other with their coatings next to each other. Pressure is exerted from the first sheet by writing by hand or by means of a typewriter, and a deep green copy develops at one on the developercoated sheet and is found to be highly light-fast.

A corresponding deep, light-fast blue or green copy is also obtained on using any other of the colour formers indicated in preparation examples 2 to 44.

EXAMPLE 46:

1 g of the phthalide of Example 6 is dissolved in 17 g of toluene. To this solution are added with stirring 12 g of polyvinyl acetate, 8 g of calcium carbonate and 2 g of titanium dioxide. The resulting suspension is diluted with toluene in a weight ratio of 1:1 and is coated with a 10 μm doctor blade onto a sheet of paper. Onto this sheet of paper is placed a second sheet of paper whose underside has been coated in an add-on weight of 3 g/m$^2$ with a mixture comprising 1 part of an amide wax, 1 part of a stearine wax and 1 part of zinc chloride. Pressure is exerted on the top sheet by writing by hand or with the means of a typewriter, and a deep and light-fast blue colour develops at once on the sheet coated with the colour former.

EXAMPLE 47:

Preparation of a heat-sensitive recording material 32 g of 4,4'isopropylidenediphenol (bisphenol A), 3.8 g of the distearylamide of ethylenediamine, 39 g of kaolin, 20 g of an 88% hydrolysed polyvinyl alcohol and 500 ml of water are bowl-milled to a particle size of about 5 μm. In a second bowl mill, 6 g of the phthalide of Example 1, 3 g of an 88% hydrolysed polyvinyl alcohol and 60 ml are milled to the particle size of about 3 μm.

The two dispersions are added together and coated in a dry add-on weight of 5.5 g/m$^2$ onto a sheet of paper. Contacting the paper with a hot ballpoint pen produces a deep green colour of excellent light and sublimation fastness.

The deep and light-fast blue or green colour can also be obtained by using any of the other colour formers of Examples 2 to 44.

EXAMPLE 48:

0.300 g of the colour former of the formula

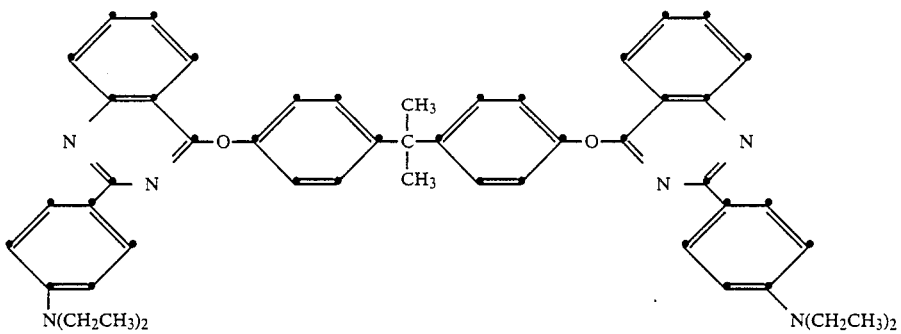

0.440 g of 3,3-bis-(N-n-octyl-2'-methylindol-3-yl)phthalide and 0.800 g of the phthalide of Example 9 are stirred into 100 g of partially hydrogenated terphenyl and dissolved at 70°–80° C. The solution obtained is applied with an intaglio printing apparatus onto a presized sheet of paper coated with activated clay. A deep black colour develops within seconds.

A similarly satisfactory result is obtained on encapsulating the colour former solution used in Example 48 as described in U.S. Pat. No. 2,800,457. The capsule mass may have further ingredients such as binder and starch. The resulting capsule dispersion is coated onto presized paper in an add-on weight of 5–7 g/m² based on the capsule material. A second sheet of paper is coated with activated clay. The sheet coated with the capsule dispersion and the sheet coated with activated clay are placed on top of each other with their coatings next to each other. Writing under pressure on the first sheet produces an exact copy on the clay-coated sheet. The copy has a black colour.

EXAMPLE 49:

0.610 g of 2-tert.-butyl-6-diethylaminofluoran, 0.900 g of the phthalide of Example 2 and 0.133 g of 3,3-bis-(4'-dimethylaminophenyl)-6-dimethylaminophthalide are stirred into 100 g of partially hydrogenated terphenyl and dissolved at 70°–80° C. The solution obtained is applied with an intaglio printing apparatus onto a presized sheet of paper coated with activated clay. A deep black colour develops within seconds.

A similarly satisfactory result is obtained on encapsulating the colour former solution used in Example 49 as described in U.S. Pat. No. 2,800,457. The capsule mass may have further ingredients such as binder and starch. The resulting capsule dispersion is coated onto presized paper in an add-on weight of 5–7 g/m² based on the capsule material. A second sheet of paper is coated with activated clay. The sheet coated with the capsule dispersion and the sheet coated with activated clay are placed on top of each other with their coatings next to each other. Writing under pressure on the first sheet produces an exact copy on the clay-coated sheet. The copy has a black colour.

What is claimed is:

1. A chromogenic phthalide or azaphthalide of the formula

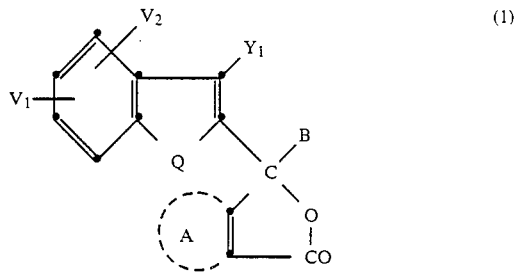

in which $V_1$ and $V_2$ are each, independently of the other, hydrogen, halogen, lower alkyl, lower alkoxy, (lower alkoxy)carbonyl or $-NR_1R_2$, at least one of the radicals $V_1$ and $V_2$ being lower alkoxy or $-NR_1R_2$, A is an unsubstituted or halogen-, cyano-, nitro-, (lower alkyl)-, (lower alkoxy)-, (lower alkyl)thio-, (lower alkyl)amino-or di(lower alkyl)amino-substituted benzene, naphthalene, pyridine, quinoline, pyrazine or quinoxaline ring, B is a substituted phenyl radical of the formula

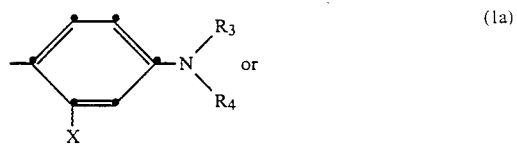

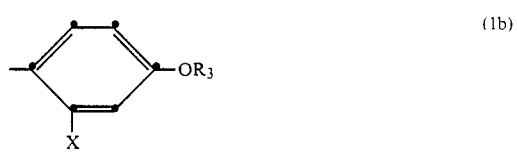

Q is

$R_1$, $R_2$, $R_3$ and $R_4$ are each, independently of the others, hydrogen, unsubstituted or halogen-, hydroxy-, cyano- or (lower alkoxy)-substituted alkyl having at most 12 carbon atoms, cycloalkyl having 5 to 10 carbon atoms or unsubstituted or halogen-, cyano-, (lower alkyl)- or (lower alkoxy)ringsubstituted phenalkyl or phenyl, or the substituent pairs ($R_1$ and $R_2$) and ($R_3$ and $R_4$) are each, independently of each other, together with the nitrogen atom joining them a five- or six-membered, heterocyclic radical, $Y_1$ is hydrogen, lower alkyl, cycloalkyl, phenalkyl or phenyl, $Z_2$ is hydrogen, unsubstituted or halogen-, hydroxyl-, cyano- or (lower alkoxy)-substituted alkyl having at most 12 carbon atoms, acyl having 1 to 12 carbon atoms or unsubstituted or halogen-, cyano-, (lower alkyl)- or (lower alkoxy)-substituted benzyl, X is hydrogen, halogen, lower alkyl, $C_1$-$C_{12}$-alkoxy, $C_1$-$C_{12}$-acyloxy, benzyl, phenyl, benzyloxy, phenyloxy, halogen-, cyano-, (lower alkyl)- or (lower alkoxy)-substituted benzyl or benzyloxy, or the group $-NT_1T_2$, $T_1$ and $T_2$ are each, independently of the other, hydrogen, lower alkyl, cycloalkyl, unsubstituted or halogen-, cyano-, (lower alkyl) or (lower alkoxy)-substituted benzyl or acyl having 1 to 12 carbon atoms and $T_1$ is also unsubstituted or halogen-, cyano-, (lower alkyl)- or (lower alkoxy)-substituted phenyl.

2. A phthalide or azaphthalide according to claim 1, wherein, in the formula (1) $V_1$ is $-NR_1R_2$ or lower alkoxy and $V_2$ is hydrogen, halogen or methyl.

3. A phthalide or azaphthalide according to claim 1, wherein, in the formula (1), $Y_1$ is lower alkyl.

4. A phthalide or azaphthalide according to claim 1, of the formula

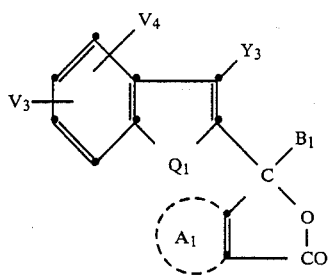 (2)

in which
$V_3$ is lower alkoxy or $-NR_5R_6$,
$V_4$ is hydrogen, halogen or lower alkyl,
$A_1$ is an unsubstituted or halogen-, cyano-, (lower alkyl)-, (lower alkoxy)- or di(lower alkyl)amino-substituted benzene or pyridine ring,
B is a substituted phenyl radical of the formula

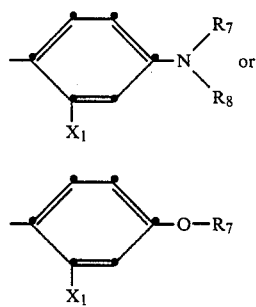 (2a)

(2b)

$Q_1$ is

$R_5$, $R_6$, $R_7$ and $R_8$ are each, independently of the others, unsubstituted or hydroxy-, cyano- or (lower alkoxy)substituted alkyl having at most 12 carbon atoms, $C_5$-$C_6$-cycloalkyl, benzyl, phenethyl or phenyl, or the substituent pairs ($R_5$ and $R_6$) and ($R_7$ and $R_8$) are each, independently of the other, together with the nitrogen atom joining them, pyrrolidino, piperidino or morpholino, $Y_3$ is lower alkyl, $C_5$-$C_6$cycloalkyl, benzyl, phenethyl or phenyl, $Z_4$ is hydrogen, unsubstituted or cyano- or (lower alkoxy)-substituted $C_1$-$C_8$-alkyl, acetyl, propionyl or benzyl, $X_1$ is hydrogen, halogen, lower alkyl, $C_1$-$C_8$-alkoxy, benzyloxy or the group $-NT_3T_4$, $T_3$ and $T_4$ are each, independently of the other, hydrogen, lower alkyl, (lower alkyl)carbonyl or unsubstituted or halogen-, methyl- or methoxy-substituted benzoyl.

5. A phthalide according to claim 4, wherein, in the formula (2), the ring $A_1$ is unsubstituted or halogen- or di(lower alkyl)amino-substituted 1,2-benzo radical.

6. A phthalide according to claim 1, of the formula

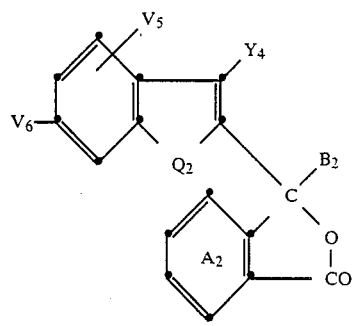 (3)

in which
the benzene ring $A_2$ is unsubstituted or substituted by a (lower alkyl)amino or halogen,
$B_2$ is a substituted phenyl radical of the formula

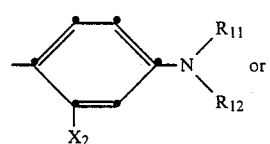 (3a)

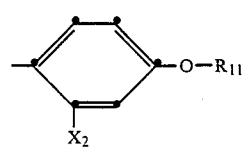 (3b)

$Q_2$ is

$V_5$ is hydrogen or halogen,
$V_6$ is $-NR_9R_{10}$ or lower alkoxy,
$R_9$, $R_{10}$, $R_{11}$ and $R_{12}$ are each, independently of the others, lower alkyl, cyclohexyl or benzyl, or the substituent groups $-NR_9R_{10}$ and $NR_{11}R_{12}$ are each, independently of the other, pyrrolidino, piperidino or morpholino, $X_2$ is hydrogen, methyl, lower alkoxy, benzyloxy, acetylamino, propionylamino, benzoylamino or di(lower alkyl)amino, $Y_5$ is lower alkyl, $Z_6$ is hydrogen, alkyl having 1 to 8 carbon atoms or benzyl.

7. A phthalide according to claim 6, wherein, in the formula (3)

A$_2$ is an unsubstituted or dimethylamino-substituted 1,2-benzo radical,
B$_2$ is a substituted phenyl radical of the formula (3a) or (3b),
Q$_2$ is

V$_5$ is hydrogen or chlorine,
V$_6$ is —NR$_9$R$_{10}$,
R$_9$ is methyl, ethyl or cyclohexyl,
R$_{10}$ is methyl or ethyl or NR$_9$R$_{10}$ is pyrrolidinyl,
R$_{11}$ and R$_{12}$ are each methyl or ethyl or —NR$_{11}$R$_{12}$ is pyrrolidinyl,
Y$_5$ is methyl or ethyl,
X$_2$ is hydrogen, methoxy or ethoxy, and
Z$_6$ is C$_1$-C$_8$-alkyl.

8. A phthalide according to claim 6, wherein in the formula (3)
A$_2$ is an unsubstituted or dimethylamino-substituted 1,2-benzo radical,
B$_2$ is a substituted phenyl radical of the formula (3a),
Q$_2$ is

V$_5$ is hydrogen or chlorine,
V$_6$ is lower alkoxy,
R$_{11}$ and R$_{12}$ are each methyl or ethyl, or —NR$_1$R$_{12}$ is pyrrolidinyl,
Y$_5$ is methyl or ethyl,
X$_2$ is hydrogen, methoxy or ethoxy and
Z$_6$ is C$_1$-C$_8$-alkyl.

9. A phthalide according to claim 8, wherein Z$_6$ is methyl, ethyl or n-octyl.

* * * * *